United States Patent
Demir

(10) Patent No.: US 10,213,154 B2
(45) Date of Patent: Feb. 26, 2019

(54) STRAIN SENSOR DEVICE WITH A BIOLOGICAL SUBSTRATE AND METHOD OF MANUFACTURING THEREOF

(71) Applicant: INNOVATIVE IN VIVO SENSING, LLC, Fort Collins, CO (US)

(72) Inventor: Hilmi Volkan Demir, Ankara (TR)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 883 days.

(21) Appl. No.: 14/656,525

(22) Filed: Mar. 12, 2015

(65) Prior Publication Data

US 2015/0216476 A1    Aug. 6, 2015

Related U.S. Application Data

(63) Continuation of application No. PCT/US2013/059555, filed on Sep. 12, 2013.
(Continued)

(51) Int. Cl.
*A61B 5/00* (2006.01)
*A61F 2/28* (2006.01)

(52) U.S. Cl.
CPC .......... *A61B 5/4851* (2013.01); *A61B 5/4504* (2013.01); *A61B 5/686* (2013.01);
(Continued)

(58) Field of Classification Search
CPC ......... H01L 23/38; H01L 25/18; H01L 27/16; H01L 2924/0002
See application file for complete search history.

(56) References Cited

U.S. PATENT DOCUMENTS

| | | |
|---|---|---|
| 5,200,051 A | 4/1993 | Cozzette et al. |
| 2002/0049394 A1* | 4/2002 | Roy ............... A61B 5/4504 600/594 |

(Continued)

FOREIGN PATENT DOCUMENTS

WO    2012112819 A2    8/2012

OTHER PUBLICATIONS

A. Hierlemann, et al., "Microfabrication Techniques for Chemical/Biosensors", Proceedings of the IEEE, Jun. 2003, pp. 839-863, vol. 91, No. 6.
(Continued)

*Primary Examiner* — Rene Towa
(74) *Attorney, Agent, or Firm* — Rossi, Kimms & McDowell LLP

(57) ABSTRACT

A strain sensor device having a biological substrate composed of a standalone bone graft or an isolated piece of bone that can be incorporated directly into, or attached to another piece of bone that is then implantable, in a biological subject, and a method thereof. The strain sensor device can includes a strain sensing circuit, which is composed of at least a first dielectric layer and a first conductive layer, that functions as a strain gauge. The first dielectric layer can be composed of dielectric material disposed over the biological substrate. The first conductive layer, which has a pattern, can be disposed over the first dielectric material. A bonding interface is disposed between the biological substrate and the first dielectric layer. The bonding interface can be composed of an underlayer of polydimethylsiloxane and a first interface layer. The underlayer can be disposed on the bone graft substrate.

19 Claims, 4 Drawing Sheets

Related U.S. Application Data

(60) Provisional application No. 61/700,162, filed on Sep. 12, 2012.

(52) U.S. Cl.
CPC ........ *A61F 2/28* (2013.01); *A61B 2562/0261* (2013.01); *A61B 2562/12* (2013.01); *A61B 2562/164* (2013.01); *A61F 2002/2835* (2013.01)

(56) References Cited

U.S. PATENT DOCUMENTS

| | | | |
|---|---|---|---|
| 2006/0247539 A1 | 11/2006 | Schugt et al. | |
| 2007/0276201 A1* | 11/2007 | Lee | A61B 5/0031 600/301 |
| 2009/0299228 A1* | 12/2009 | Lozier | A61B 17/7275 600/587 |
| 2010/0132476 A1* | 6/2010 | Cheng | G01B 7/18 73/774 |
| 2010/0294041 A1 | 11/2010 | Tai et al. | |
| 2011/0152725 A1 | 6/2011 | Demir et al. | |
| 2012/0197155 A1 | 8/2012 | Mattes et al. | |
| 2014/0238153 A1* | 8/2014 | Wood | G06F 3/011 73/862.627 |
| 2014/0243703 A1 | 8/2014 | Schmidt et al. | |

OTHER PUBLICATIONS

International Search Report issued in PCT/US2013/059555, dated Dec. 13, 2013.
Written Opinion issued in PCT/US2013/059555, dated Dec. 13, 2013.

\* cited by examiner

STRAIN SENSOR DEVICE WITH A BIOLOGICAL SUBSTRATE AND METHOD OF MANUFACTURING THEREOF

CROSS REFERENCE

This is a continuation of PCT/US2013/59555 filed 12 Sep. 2013, which claims priority to U.S. Provisional Application Ser. No. 61/700,162 filed 12 Sep. 2012. The entire disclosures of the PCT and Provisional Applications are herein incorporated by reference.

BACKGROUND

USPGP 2011/0152725 published Jun. 23, 2011 discloses a wireless resonator sensor circuitry, composed of a dielectric material and a conductive coil that functions as a strain gauge. The detailed description of the resonator sensor circuitry disclosed in USPGP 2011/0152725 is herein incorporated by reference.

SUMMARY

The present invention relates to a strain sensor device that can temporally measure the strain on the graft and predict the healing potential of the graft, and a method of manufacturing the strain sensor device.

One aspect of the present invention is the strain sensor device having a biological substrate composed of a (stand-alone) bone graft or an isolated piece of bone that can be incorporated directly into, or attached to another piece of bone that is then implantable, in a biological subject.

The sensor can be an inductively-powered telemetric wireless sensor (i.e., no battery source) that can be directly deposited on the biological substrate.

The strain sensor device can include a strain sensing circuit (strain sensing elements), which is composed of a first dielectric layer and a first conductive layer, that functions as a strain gauge. The first dielectric layer can be composed of dielectric material disposed over the biological substrate. The first conductive layer, which has a pattern, can be disposed over the first dielectric material.

A bonding interface can be disposed between the biological substrate and the first dielectric layer, which can be composed of silicon nitride. The bonding interface can be composed of an underlayer of polydimethylsiloxane (PDMS) or other biocompatible dielectric material and a first interface layer. The underlayer can be disposed on the bone graft substrate. The first interface layer can be disposed on the underlayer.

The strain sensing circuit can further include a second dielectric layer composed of silicon nitride and a second conductive layer. The second dielectric layer and the second conductive layer can be disposed between the first interface layer and first dielectric layer.

The strain sensor device can further include a second interface layer and a third interface layer. The second dielectric layer can be disposed on the first interface layer. The second interface layer can be disposed on the second dielectric layer. The second conductive layer can be disposed on the second interface layer. The third interface layer can be disposed on the second conductive layer. The first dielectric layer can be disposed on the third interface.

The strain sensor device can further include a fourth interface layer, which can be disposed on the first dielectric layer. The first conductive layer can be disposed on the fourth interface layer.

Each of the first, second, third, and fourth interface layers can be composed of titanium. The underlayer can have a thickness of 10 μm. Each of the first, second, third, and fourth interface layers can have a thickness of 10 nm. Each of the first and second dielectric layers can have a thickness of 100 nm. Each of the first and second conductive layers can have a thickness of 100 nm.

Another aspect of the present invention is a method of manufacturing the above strain device. The method can include the steps of cleaning the bone graft substrate, depositing the bonding interface on the cleaned bone graft substrate, and depositing the strain sensing circuit on the bonding interface.

The method can further include the steps of mixing the PDMS material and a curing agent at a ratio of 10:1 in weight, degassing the mixture of the PDMS material and the curing agent for a predetermined time, spin-coating the mixture to form the PDMS layer having a thickness of 10 μm on the cleaned biological substrate, and baking the biological substrate with the PDMS layer to thermally cure the PDMS underlayer.

The method can further include the steps of depositing the underlayer on the bone graft substrate, depositing the first interface layer on the underlayer, and depositing the second dielectric layer and the second conductive layer in this order between the first interface layer and first dielectric layer.

The method can further include the steps of depositing the second dielectric layer on the first interface layer, depositing the second interface layer on the second dielectric layer, depositing the second conductive layer on the second interface layer, and depositing the third interface layer on the second conductive layer.

The method can further include the step of depositing the first dielectric layer on the third interface, depositing the fourth interface layer on the first dielectric layer, and depositing the first conductive layer on the fourth interface layer.

DETAILED DESCRIPTION

The present strain sensor 1 can be directly printed (i.e., deposited) on a bone graft and temporally measure the strain on the bone graft and predict the healing potential of the bone graft, and is an inductively-powered telemetric wireless sensor (i.e., no battery source).

Figure 1:
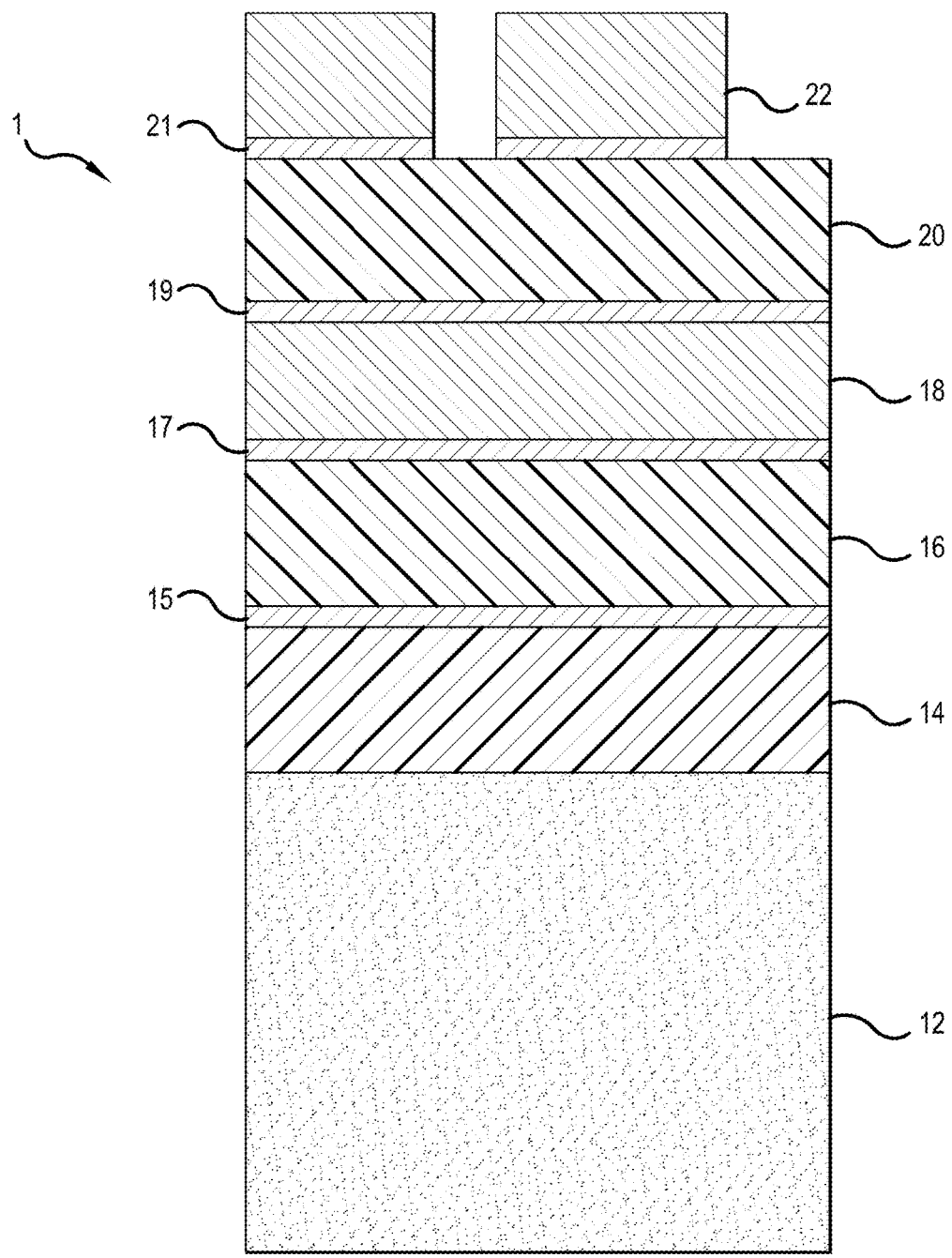
FIG. 1 schematically illustrates a cross-section of one embodiment of a fabricated wireless strain sensor on the bone graft.

Referring to FIG. 1, the strain sensor 1 comprises a biological substrate 12, namely a bone graft, a strain sensing circuit that functions as a strain gauge, namely sensing strain applied to the substrate, and a bonding interface that improves bonding between the substrate 12 and the strain sensing circuit. The use of the term "lower" and "upper" refer to in relation to the orientation of the strain sensor illustrated in FIG. 1.

The strain sensing circuit can be composed of a layer 20 of a dielectric film, which can be, for example, silicon nitride, and a conductive layer 22 of conductive metal film that is patterned, such as in a form of a coil, ring, or a comb-shaped configuration (see FIG. 2, Image C) that functions as a resonating strain gauge. The strain sensing circuit can be a resonator strain sensing circuit, such as disclosed in USPGP 2011/0152725.

The bonding interface can include one or more layers 14, 15 of different materials that enhance adhesion properties of the strain sensing circuit to the underlying bone graft substrate 12. Specifically, the bonding interface can be composed of an underlayer 14 of polydimethylsiloxane (PDMS) or other biocompatible dielectric material and an interface layer 15, which can be a titanium film, to ensure that the dielectric layer 16, 20 bonds to the underlying PDMS underlayer 14.

The strain sensor 1 can further include a sensor enhancing interface, which can be composed of layers 16, 18. Specifically, the sensor enhancing interface can be composed of a lower dielectric layer 16 and a lower conductive layer 18. The lower conductive layer 18 serves as a ground plane to capacitively couple the resonator in the strain sensing circuit to tune its resonance frequency. The lower conductive layer thus functions as a conductive substrate.

To enhance adhering properties between the adjoining layers 14, 16, 18, 20, and 22, an interface layer 15, 17, 19, and 21 can be adhered between the adjoining layers, as illustrated in FIG. 1. Each of the interface layers can be composed of titanium.

Each of the metal layers 18 and 22 can be made of gold or gold containing metal to enhance conductivity.

Each of the dielectric layers 16, 20 can be made of silicon nitride ($Si_3N_4$), which is a solid material that undergoes strain when the bone graft substrate undergoes strain.

The strain sensor 1 can be fabricated using conventional lithographic and MEMs techniques. In this respect, see the disclosures of U.S. Pat. No. 5,200,051 issued 6 Apr. 1993 to Cozzette, et al., the disclosure of which is herein incorporated by reference, and *Microfabrication Techniques for Chemical/Biosensors* by Hierlemann, et al.

Nonetheless, this is the first time that a strain sensing circuit has been successfully printed on a biological substrate. In addition, the present development obviates the need for an interfacial layer (usually glue, such as an epoxy) needed to attach the sensor to an implantable hardware.

The strain sensor fabrication process involves cleaning the bone graft, coating the cleaned bone graft to make it suitable for microfabrication of the strain sensing circuit (namely depositing the bonding interface 14, 15) on a cleaned bone graft and depositing the strain sensing circuit over the bonding interface.

Specifically, the following method steps can be used to fabricate the bone graft strain sensor 1 illustrated in FIG. 1. First, the bone graft is cleaned to ensure that all solute chemicals, dust, and other contaminants are removed from the bone graft. The bone graft can be sonicated in water, acetone, and isopropanol, for 10 min each. Subsequently, the sonicated bone graft can be baked on a hot plate at 150° C. for 15 min in a cleanroom environment.

Next, the cleaned bone graft is first coated with a mixture of PDMS material (Slygard 184) and a curing agent. The mixture can be prepared with a ratio of 10:1 (PDMS:curing agent) in weight. After mixing, the mixture can be degassed in a desiccator about 15 min. The cleaned bone graft can be spin-coated with the prepared PDMS mixture at 2500 rpm for 5 min. This results in an underlayer 14 of a PDMS film thickness of 10 µm on the cleaned bone graft. The desired thickness of the PDMS film is in the range of hundreds of nanometers to tens of micrometers. Then, the coated bone graft can be baked on a hot-plate at 150° C. for 15 min to thermally cure the PDMS film.

Next, after curing the PDMS underlayer 14, the first interface layer 15 can be deposited, namely sputtered, to achieve about a 10 nm thick titanium film to ensure that the subsequent coating, namely the lower (second) dielectric layer 16 (silicon nitride film ($Si_xN_y$) adheres to the bone graft substrate via the underlayer 14.

Next, after depositing the first interface layer 15, the dielectric layer 16 (silicon nitride) of about 100 nm can be deposited on the first interface layer 15 via conventional plasma enhanced chemical vapor deposition.

Next, layers 17, 18, 19 of Ti—Au—Ti films, namely the second interface layer 17, the lower (second) conductive layer 18, and the third interface layer, can be thermally evaporated on the lower (second) dielectric layer 16 with a film thickness of 10, 100, and 10 nm, respectively, in this order, using a conventional thermal evaporation system.

Next, the upper (first) dielectric layer 20 of silicon nitride film having approximately 100 nm in thickness can be deposited, for example by plasma enhanced chemical vapor deposition or any other known deposition technique, over the third interface layer 19.

Next, layers 21, 22 of Ti—Au films with a film thickness of 10 and 100 nm, respectively, namely the fourth interface layer 21 and the upper (first) conductive layer 22 can be thermally evaporated on the upper dielectric layer 20.

Next, lithography can be performed on the top layer, namely the upper conductive layer 22, to pattern the sensor structure thereon, which pattern can be a coil or ring, comb-shape, using conventional lithography and metal lift-off (i.e., etching) of the fourth interface layer 21 and the upper conductive layer 22 to form the patterned conductive layers 21, 22.

Figure 2:
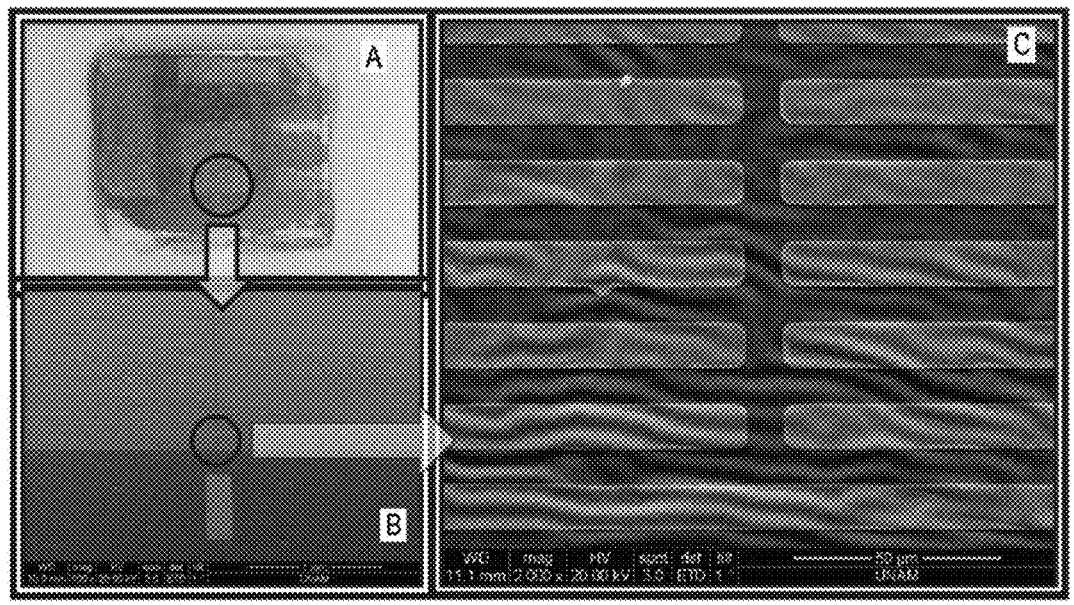
FIG. 2 illustrates Images A-C, where Image A is an optical microscopy image of the top view of the sensor schematically illustrated in FIG. 1, Image B is a scanning electron microscopy (SEM) image showing a circuit portion of the sensor shown in image A, and Image C is an SEM image showing an enlarged portion of black circle marked on image B.
Figure 3:
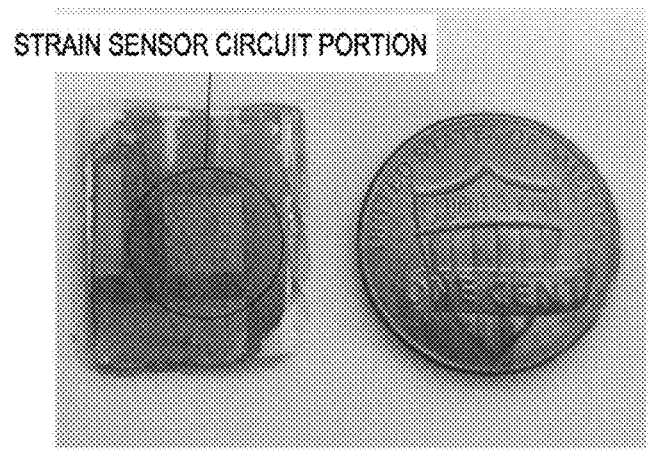
FIG. 3 illustrates an image of the sensor illustrated in Image A in relation to a one cent U.S. coin for a dimensional comparison.

FIGS. 2 and 3 show the images of the microfabricated strain sensor 1, with the overall sensor chip layout having 8 mm×8 mm. In FIG. 2, Image A is an optical microscopy image of the top view of the sensor schematically illustrated in FIG. 1, Image B is a scan electron microscopy (SEM) image showing a circuit portion, namely the patterned top layer 22 of the sensor shown in image A, and Image C is an SEM image showing an enlarged portion of black circle marked on image B, showing the patterned conductive layer 22 in a comb-shaped configuration. FIG. 3 illustrates an image of the sensor illustrated in Image A in relation to a one cent U.S. coin for a dimensional comparison.

Figure 4:
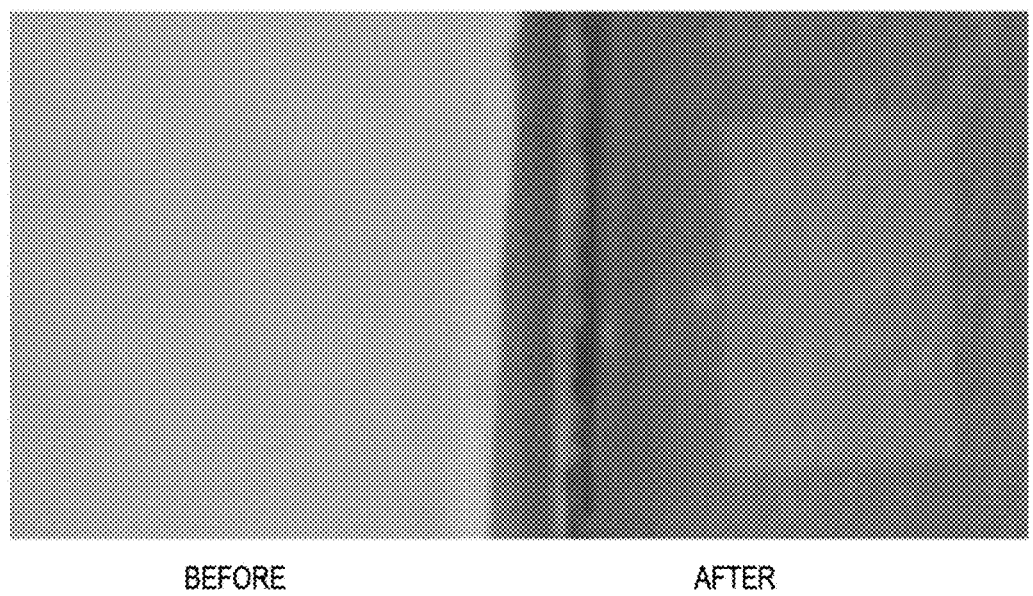
FIG. 4 is an optical microscopy image of a top view of a bone graft before and after fabricating the sensor on the bone graft.
Figure 5:
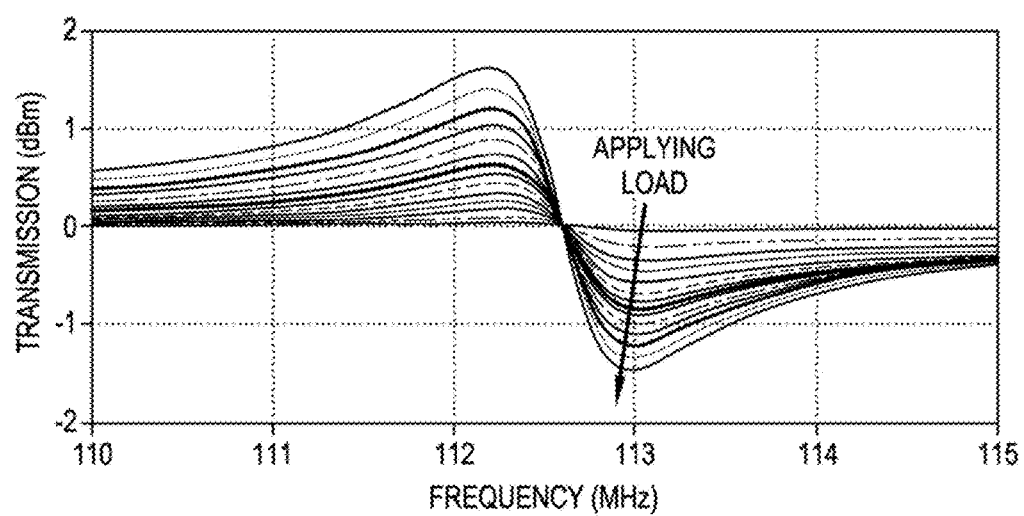
FIG. 5 illustrates a graph showing a frequency scan that shows the strain propagation properties being significantly elevated due to an attachment layer being omitted.
Figure 6:
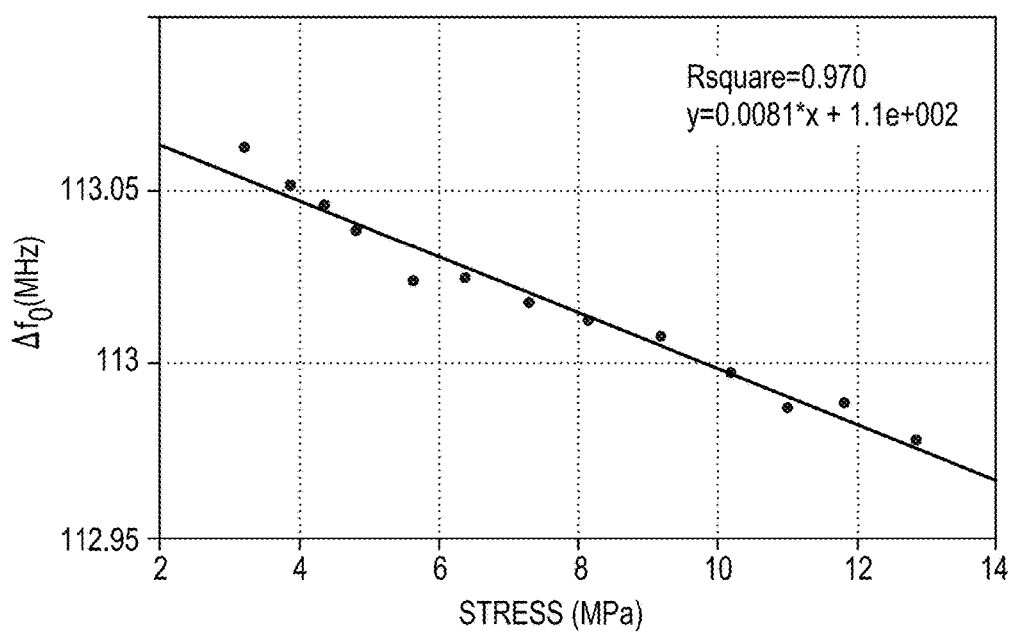
FIG. 6 illustrates wireless sensing characterization with an external mechanical loading based on the resonance frequency shift as a function of induced strain (here the calibration is performed with respect to the unloaded case).

FIG. 4 shows an optical microscopy image of a top view of a bone graft before and after fabricating the sensor on the bone graft. FIG. 5 illustrates a graph showing a frequency scan that shows the strain propagation properties being significantly elevated due to an attachment layer being omitted. FIG. 6 illustrates wireless sensing characterization with an external mechanical loading based on the resonance frequency shift as a function of induced strain. The calibration was performed with respect to the unloaded case in FIG. 6.

The present strain sensor 1 does not have any conventional substrate for manufacturing a circuit chip. Rather, it uses a bone graft as a substrate, which obviates the need for any attachment hardware. This beneficially improves strain gauge sensitivity. Indeed, the strain propagation properties beneficially become significantly elevated when the attachment layer, including the interfacial layer, is omitted. See FIGS. 5 and 6.

The present bone graft strain sensor 1 has a higher sensitivity to strain than a silicon based rigid strain sensor when they are both attached onto a deforming platform, due to the much lower elastic modulus of the bone as compare to a silicon or comparable substrate.

Given that the sensor is rigidly attached to the loading member, which is the case here since the sensor circuit is deposited and formed directly on the bone graft substrate 12, the strain ($\epsilon_{substrate}$) imparted to the bone graft substrate 12, on which the sensing elements are directly deposited or imprinted thereon, is substantially similar to the strain that the sensing element, namely the dielectric layer 16, experiences ($\epsilon_{sensor}$):

$$\epsilon_{substrate} \approx \epsilon_{sensor}.$$

From linear elasticity, the normal stress ($\sigma$) experienced by a material is equal to the product of the material's stiffness (i.e., elastic or Young's modulus, E), and the strain ($\epsilon$) it experiences can be represented as:

$$\frac{\sigma_{substrate}}{E_{substrate}} = \frac{\sigma_{sensor}}{E_{sensor}} = \epsilon_{sensor}.$$

Therefore, the ratio of the stress to the stiffness should be substantially constant between the substrate and the sensor:

$$\sigma = E\epsilon \text{ or } \epsilon = \frac{\sigma}{E}.$$

Therefore, the strain experienced by the strain sensing circuit, for the same amount of load or strain applied, is increased in proportion to the decrease in the sensor's elastic modulus $\epsilon_{sensor}$. Therefore, since bone's elastic modulus=10 GPa, which is much less than the elastic modulus of silicon (E=167 GPa), the present bone graft strain sensor 1 will provide better sensitivity than a silicon substrate based sensor.

In sum, the present strain sensor 1, which has a bone graft sensor fabricated directly on the bone graft substrate (with no additional substrate) has a greater sensitivity than a silicon substrate based sensor due to the bone graft substrate having a much smaller elastic modulus, namely in the order of 16 times less.

All modifications and equivalents attainable by one of ordinary skill in the art from the present disclosure within the scope and spirit of the present invention are to be included as further embodiments of the present invention. It is to be understood that the above description is intended to be illustrative, and not restrictive, and that the phraseology or terminology employed herein is for the purpose of description. The scope of the present accordingly is to be defined as set forth in the appended claims.

What is claimed is:

1. A strain sensor device implantable in a biological subject, the strain sensor device comprising:
   a biological substrate composed of a bone graft;
   a first dielectric layer composed of dielectric material disposed over the biological substrate;
   a bonding interface, composed of an underlayer and a first interface layer, disposed between the biological substrate and the first dielectric layer, the underlayer being disposed on the biological substrate and the first interface layer being disposed on the underlayer;
   a first conductive layer having a pattern disposed over the first dielectric material; and
   a second dielectric layer;
   a second conductive layer,
   wherein the second dielectric layer and the second conductive layer are disposed between the first interlace layer and the first dielectric layer; and
   a strain sensing circuit, composed of the first dielectric layer, the first conductive layer, the second dielectric layer, and the second conductive layer, that functions as a strain gauge.

2. The strain sensor device according to claim 1, wherein the underlayer is composed of polydimethylsiloxane (PDMS).

3. The strain sensor device according to claim 2, wherein the first dielectric layer is composed of silicon nitride.

4. The strain sensor device according to claim 3, wherein the second dielectric layer is composed of silicon nitride.

5. The strain sensor device according to claim 4, further including:
   a second interface layer; and
   a third interface layer,
   wherein the second dielectric layer is disposed on the first interface layer,
   wherein the second interface layer is disposed on the second dielectric layer,
   wherein the second conductive layer is disposed on the second interface layer, and
   wherein the third interface layer is disposed on the second conductive layer.

6. The strain sensor device according to claim 5, wherein the first dielectric layer is disposed on the third interface.

7. The strain sensor device according to claim 6, further including:
   a fourth interface layer,
   wherein the fourth interface layer is disposed on the first dielectric layer, and
   wherein the first conductive layer is disposed on the fourth interface layer.

8. The strain sensor device according to claim 7, wherein each of the first, second, third, and fourth interface layers is composed of titanium.

9. The strain sensor device according to claim 8, wherein:
   the underlayer has a thickness of 10 μm,
   each of the first, second, third, and fourth titanium interface layers has a thickness of 10 nm,
   each of the first and second dielectric layers has a thickness of 100 nm, and
   each of the first and second conductive layers has a thickness of 100 nm.

10. A method of manufacturing a strain sensor device implantable in a biological subject, the strain sensor device comprising:
    a biological substrate composed of a bone graft;
    a first dielectric layer composed of dielectric material disposed over the biological substrate;

a bonding interface, composed of an underlayer of polydimethylsiloxane (PDMS) and a first interface layer, disposed between the biological substrate and the first dielectric layer;
a first conductive layer having a pattern disposed over the first dielectric material; and
a strain sensing circuit, composed of the first dielectric layer and the first conductive layer, that functions as a strain gauge,
wherein the method comprises the steps of:
cleaning the biological substrate;
mixing a PDMS material and a curing agent at a ratio of 10:1 in weight;
degassing the mixture of the PDMS material and the curing agent for a predetermined time;
depositing the mixture on the cleaned biological substrate by spin-coating the mixture on the cleaned biological substrate;
baking the biological substrate with the deposited mixture to thermally cure the underlayer; and
depositing the strain sensing circuit on the bonding interface.

11. The method according to claim 10, wherein the mixture depositing step deposits the mixture having a thickness of 10 μm on the cleaned biological substrate.

12. The method according to claim 11, wherein the first dielectric layer is composed of silicon nitride.

13. The method according to claim 12, further comprising the steps of:
depositing the underlayer on the biological substrate;
depositing the first interface layer on the underlayer,
wherein the strain sensing circuit further includes a second dielectric layer composed of silicon nitride and a second conductive layer, and
depositing the second dielectric layer and the second conductive layer in this order between the first interface layer and first dielectric layer.

14. The method according to claim 13, wherein:
the strain sensor device further includes a second interface layer and a third interface layer, and
the method further includes the steps of:
depositing the second dielectric layer on the first interface layer;
depositing the second interface layer on the second dielectric layer;
depositing the second conductive layer on the second interface layer; and
depositing the third interface layer on the second conductive layer.

15. The method according to claim 14, further comprising the step of depositing the first dielectric layer on the third interface.

16. The method according to claim 15, wherein:
the strain sensor device further includes a fourth interface layer, and
the method further includes the steps of:
depositing the fourth interface layer on the first dielectric layer; and
depositing the first conductive layer on the fourth interface layer.

17. The method according to claim 16, wherein each of the first, second, third, and fourth interface layers is composed of titanium.

18. The method according to claim 17, wherein:
each of the first, second, third, and fourth titanium interface layers has a thickness of 10 nm,
each of the first and second dielectric layers has a thickness of 100 nm, and
each of the first and second conductive layers has a thickness of 100 nm.

19. A method of manufacturing a strain sensor device implantable in a biological subject, the strain sensor device comprising:
a biological substrate composed of a bone graft;
a first dielectric layer composed of dielectric material disposed over the biological substrate;
a bonding interface, composed of an underlayer and a first interface layer, disposed between the biological substrate and the first dielectric layer, the underlayer being disposed on the biological substrate and the first interface layer being disposed on the underlayer;
a first conductive layer having a pattern disposed over the first dielectric material; and
a second dielectric layer;
a second conductive layer,
wherein the second dielectric layer and the second conductive layer are disposed between the first interface layer and the first dielectric layer; and
a strain sensing circuit, composed of the first dielectric layer, the first conductive layer, the second dielectric layer, and the second conductive layer, that functions as a strain gauge,
wherein the method comprises the steps of:
cleaning the biological substrate;
depositing the bonding interface on the cleaned biological substrate; and
depositing the strain sensing circuit on the bonding interface.

* * * * *